(12) United States Patent
Saksena et al.

(10) Patent No.: US 8,829,157 B2
(45) Date of Patent: *Sep. 9, 2014

(54) PROCESS FOR THE SYNTHESIS OF CYCLIC HEPTAPEPTIDE

(75) Inventors: Divya Lal Saksena, Mumbai (IN);
Chandrakesan Muralidharan, Mumbai (IN); Lester Lobo, Mumbai (IN);
Digamber Shripati Pawar, Mumbai (IN); Nikhil Umesh Mohe, Mumbai (IN); Radhakishnan Venkatasubramanian Tarur, Mumbai (IN)

(73) Assignee: USV, Ltd., Mumbai (IN)

( * ) Notice: Subject to any disclaimer, the term of this patent is extended or adjusted under 35 U.S.C. 154(b) by 671 days.

This patent is subject to a terminal disclaimer.

(21) Appl. No.: 13/007,736

(22) Filed: Jan. 17, 2011

(65) Prior Publication Data

US 2011/0118437 A1    May 19, 2011

Related U.S. Application Data

(63) Continuation-in-part of application No. 11/729,047, filed on Mar. 27, 2007, now Pat. No. 7,897,724, which is a continuation-in-part of application No. 10/592,118, filed as application No. PCT/IN2004/000315 on Oct. 10, 2004, now abandoned.

(30) Foreign Application Priority Data

Jun. 14, 2004  (IN) ........................ 648/MUM/2004
Sep. 9, 2010   (IN) ........................ 2504/MUM/2010

(51) Int. Cl.
| | | |
|---|---|---|
| *A61K 38/12* | (2006.01) |
| *C07K 5/00* | (2006.01) |
| *C07K 7/00* | (2006.01) |
| *C07K 16/00* | (2006.01) |
| *C07K 17/00* | (2006.01) |
| *C07K 14/75* | (2006.01) |
| *C07K 14/78* | (2006.01) |
| *C07K 7/06* | (2006.01) |
| *A61K 38/00* | (2006.01) |

(52) U.S. Cl.
CPC . *C07K 14/75* (2013.01); *C07K 7/06* (2013.01); *A61K 38/00* (2013.01); *C07K 14/78* (2013.01)
USPC ........................................................ 530/321

(58) Field of Classification Search
CPC .................................. C07K 7/06; A61K 38/00
See application file for complete search history.

(56) References Cited

U.S. PATENT DOCUMENTS

2007/0249806 A1 * 10/2007 Saksena et al. ............... 530/317

FOREIGN PATENT DOCUMENTS

EP             2119724 A1 * 11/2009

OTHER PUBLICATIONS

O'shea et al., Expert Opin. Pharmacother., 2002, 3(8), 1199-1200.*
Xiong et al., Journal of Xiamen University, Natural Science, Jan. 2007, vol. 46, No. 1, p. 100-103.*
Fields et al., Methods in Molecular Biology, vol. 35, Peptide Synthesis Protocols, 1994, p. 29-40.*
Kawamoto, "Targeting the BCL9/B9L Binding Interaction with β-catenin as a Potential Anticancer Strategy", dissertation, The University of Michigan, 2010, available Jun. 3, 2010.*
Kirihara et al., Synthesis 2007, No. 21, pp. 3286-3289.*
Vydac's "The Handbook of Analysis and Purification of Peptides and Proteins by Reversed-Phase HPLC", third edition, 2002.*
Long et al., Preparative HPLC Scale-Up of Antibiotics, Agilent Technologies. Inc., 2004.*

* cited by examiner

*Primary Examiner* — Marcela M Cordero Garcia
*Assistant Examiner* — Kaipeen Yang
(74) *Attorney, Agent, or Firm* — Pharmaceutical Patent Attorneys, LLC (57) ABSTRACT

The present invention relates to an improved process for the large scale synthesis of cyclic heptapeptide using Fmoc solid phase synthesis technique. The described process assembles the peptide on a solid support resin by coupling to one another by peptide bonds to obtain a peptide wherein the coupling of cysteine to the resin employs a combination of solvents to reduce cysteine racemization. The process described relates to the use of C1-C4 alcohols as total substitute to organic nitriles thus making the process cost effective, non-toxic and eco-friendly.

4 Claims, 5 Drawing Sheets

PROCESS FOR THE SYNTHESIS OF CYCLIC HEPTAPEPTIDE

RELATED PATENT APPLICATIONS

The present invention is a continuation in part of U.S. patent application Ser. No. 11/729,047 filed 27 Mar. 2007, now U.S. Pat. No. 7,897,724, issued on 1 Mar. 2011, which is a continuation in part of U.S. patent application Ser. No. 10/592,118, filed 15 Aug. 2007, which claims priority from PCT International Application Serial No. PCT/IN2004/000315, which claims priority from Indian Provisional Application 648/MUM/2004, filed 14 Jun. 2004. The present invention also claims priority from Indian Provisional Application 2504/MUM/2010, filed 9 Sep. 2010; all of which are incorporated herein by reference in their entireties.

FIELD OF THE INVENTION

The present invention relates to a novel process for preparing Eptifibatide. The invention preferably relate a process for large scale synthesis of Eptifibatide using C1-C4 alcohols as total substitute to organic nitriles thus making the process cost effective, non-toxic and eco-friendly.

BACKGROUND OF THE INVENTION

Eptifibatide is a cyclic heptapeptide used for the treatment of cardio vascular disease. It is a short acting parenteral anti-thrombotic drug used for treating Acute Coronary Syndrome (ACS). It is also used in patients undergoing Percutaneous Coronary Intervention (PCI). Eptifibatide is an anti-platelet agent with high affinity and specificity for the Glycoprotein (GP) IIb/IIIa receptor that mediates platelet aggregation. Eptifibatide is an inhibitor of platelet aggregation and belongs to a new class of RGD mimetics-arginine (R), glycine (G), aspartic acid (D). Eptifibatide reversibly inhibits platelet aggregation by preventing the binding of fibrinogen, von Willebrand factor and other adhesive ligands to the GP IIb/IIIa receptors.

Eptifibatide is commercially available in United States under the brand name of Integrilin which is indicated for the prevention of early myocardial infarction in patients presenting with unstable angina or non-Q-wave myocardial infarction with the last episode of chest pain occurring within 24 hours and with ECG changes and/or elevated cardiac enzymes. Integrilin is intended for use with acetylsalicyclic acid and unfractionated heparin.

Integrilin is formulated as a sterile solution for intravenous (IV) injection in a single dose of 20 mg/10 ml vial, and as a sterile solution for IV continuous infusion of 75 mg/100 ml vial. The recommended dose is an intravenous bolus of 180 µg/kg administered as soon as possible following diagnosis, followed by a continuous infusion of 2 µg/kg for upto 72 hours (96 hours in patients undergoing coronary angioplasty).

Eptifibatide is chemically synthesized and is a cyclic heptapeptide containing six aminoacids and one thioalkyl carboxylic acid (desamino cysteinyl) residue. The active ingredient is a cyclic heptapeptide that has a molecular weight of 831.96 daltons. It is soluble in water, methanol and ethanol.

Over the years, short synthetic peptides have gained great therapeutic significance in treating life threatening diseases. Eptifibatide, Bivalirudin, Enfuviritide, and Exenatide are some of them.

Market faces the challenge to produce peptides in Kilo quantities and greater than 100 kilograms. In terms of peptide synthesis methodology, two major synthetic techniques dominate current practice. These are solution phase, and solid-phase syntheses.

The Fmoc strategy of solid phase peptide synthesis and orthogonal protection groups opened the door for the rapid synthesis of long peptides wherein physical-chemical properties are controlled, the process is amicable to automation and scalable, and no isolation of intermediates is required with short production cycles. But expensive raw materials generating a complex impurity profile are constant threats to techno-commercial processes.

At present the proven scalability of peptide chemistry is upto 1000 L reactors. The supplier customer relationship is becoming more and more complex requiring an intensive collaboration throughout the whole life cycle of product. The high volume high value peptide such as bivalirudin and Eptifibatide drive very few established API manufacturers such as Lonza and Peptisyntha due to large scale market size with an estimated API demand of 100 kilos and commercial viability of the process.

The Eptifibatide product patent expiry is targeted in US in September 2015. There is Para IV filed by Teva against the Orange Book listed method of use patents. In the current scenario, to tackle the increasing market growth and to cater the demand, an efficient cost-effective process for synthesis of Active Pharmaceutical Ingredient is the need of the hour.

The present invention targets a cost-effective novel strategy for large scale synthesis of this cyclic heptapeptide i.e. Eptifibatide acetate. The present invention relates to a process for large scale synthesis of Eptifibatide using C1-C4 alcohols as total substitute to organic nitriles thus making the process cost effective, non-toxic and eco-friendly.

OBJECT OF THE PRESENT INVENTION

The primary object of the invention relates to a process for solid phase synthesis of Eptifibatide using Fmoc strategy. More preferably another object of the invention is a process for large scale synthesis of Eptifibatide using C1-C4 alcohols as total substitute to organic nitriles thus making the process cost effective, non-toxic and eco-friendly. Still more preferably, another object of the invention is an improved process for synthesis of heptapeptide with one unnatural amino acid and one thioalkyl carboxylic acid

SUMMARY OF THE INVENTION

One aspect of the invention is a process for the large scale preparation of Eptifibatide (Formula 1) by Fmoc solid phase synthesis technique, Formula 1 the said process comprising:
a) assembling a peptide chain consisting of six amino acids and a thioalkyl carboxylic acid in a required sequence on a solid support resin by coupling to one another by peptide bonds to obtain a peptide bound resin as given below, Mpa(trt)-Har(Pbf)-Gly-Asp(Otbu)-Trp-Pro-Cys(trt)- Resin wherein the coupling of cysteine to the resin employs a combination of coupling solvents to reduce cysteine racemization;

b) cleaving from the resin and deprotecting all the protecting groups with 87.5% TFA, 2.5% TIS, 5% DTT and 5% H₂O to give SH-Eptifibatide;

c) treating the peptide with hydrogen peroxide leading to instant oxidation obtaining Eptifibatide of formula 1 and  d) purifying the crude Eptifibatide of step c) by RP-HPLC to >99% purity by using C1-C4 alcohol wherein the binding capacity of C1-C4 alcohol is 3-5 fold over organic nitrile used.

Another aspect of the invention is a process comprising the steps of:

a) manufacturing crude Eptifibatide by coupling of first Fmoc protected cysteine to the solid support using a combination of coupling solvent;

b) assembling the heptapeptide on the solid support, deprotecting, cleaving and oxidizing the heptapeptide to Eptifibatide using hydrogen peroxide;

c) purifying and polishing the crude Eptifibatide to a purity of >99% by chromatography using C1-C4 alcohols wherein the binding capacity of peptide to silica increases by 3-5 fold and  d) buffer exchanging to adjust the acetate concentration and lyophilizing the Eptifibatide acetate.

DETAILED DESCRIPTION OF THE INVENTION

Glossary of Terms Used in the Specification

Acm: Acetamidomethyl
Asp: Aspartic acid
Boc: tert-butyloxycarbonyl
Cys: Cysteine
DCM: Dichloromethane
DMF: Dimethyl Formamide
DTT: Dithiothreitol
Fmoc: 9-fluorenylmethyloxycarbonyl
Gly: Glycine
Har: Homoarginine
HBTU: 2-(1H-Benzotriazole-1-yl)-1,1,3,3-tetramethyluronium hexafluorophosphate
Mpa: Mercaptopropionic acid; Thioalkyl carboxylic acid
NMM: N-methyl morpholine
Pbf: 2,2,4,6,7-pentamethyldihydrobenzofuran-5-sulfonyl
Pro: Proline
RP-HPLC: Reverse Phase High Performance Liquid Chromatography
TFA: Trifluoroacetic acid
TIS: Triisopropylsilane
Trt: Trityl A considerable number of known, naturally occurring small and medium-sized cyclic peptides as well as some of their synthetic derivatives and analogs possessing desirable pharmacological properties have been synthesized, However, wider medical use is often hampered due to complexity of their synthesis and purification of peptides to pharmaceutical grade. Therefore improved methods for making these compounds in simple, minimum steps and in a cost effective manner is desirable and it is the need of the industry.

The purity and yield of the peptides are important aspects of any route of synthesis. The trace amounts of impurities present in the peptide may disturb and adversely affect the beneficial action of the peptide when used as a therapeutic agent. In solution phase synthesis repeated purification at each step invariable leads to low yield of the final peptide. The present invention is a novel process to achieve high purity with enhanced yield of the target peptide Eptifibatide through solid phase methodology. Callens discloses in the IBC talk, San Diego, 1999, a method of manufacturing Eptifibatide.

Scarborough et al., U.S. Pat. No. 5,686,571 discloses laboratory-scale chromatography of Eptifibatide by reversed phase HPLC using a gradient of acetonitrile in trifluoroacetic acid, wherein the chromatography fractions are directly lyophilized.

Using acetonitrile has cost impact on the overall process and also adds to the cost in being compliant to match the ICH levels of residual organic solvents.

Reported synthetic approaches to Eptifibatide have employed known techniques of solution-phase synthesis as described for example in US patent publication no. 2006/0036071A and U.S. Pat. No. 5,506,362.

U.S. Pat. Nos. 5,318,899 and 5,958,732 claim recombinant techniques to produce peptides like Eptifibatide. The peptide obtained by this recombinant process is modified by the conversion of lysine residue to homoarginine residue. These patent documents also claim solid-phase synthesis using Boc chemistry.

U.S. Pat. No. 5,759,999, U.S. Pat. No. 576,333, U.S. Pat. No. 5,770,564, U.S. Pat. No. 5,807,825, U.S. Pat. No. 5,807,828, U.S. Pat. No. 5,843,897, U.S. Pat. No. 5,968,902, U.S. Pat. No. 5,935,926, U.S. Pat. No. 5,344,783, U.S. Pat. No. 5,780,595 and U.S. Pat. No. 5,851,839 details the synthesis process for Eptifibatide employing the solid phase Boc chemistry.

The solid phase synthesis using Fmoc chemistry is known to be universally milder in nature and employs orthogonal protecting groups thus resulting in better process overall yields and cuts down to the overall turnover time.

Fmoc based solid phase syntheses are described in WO2005/121164, WO2003/093302, WO 2006045483, WO 2006/119388, WO 2006/0420, WO 2004/092202 and WO 2003/093302.

PCT publications WO 2006/119388, WO 2006/0420, and WO 2004/092202 from Novetide/Teva describe the preparation using trityl protected thioalkyl carboxylic acid and on trityl resin.

CN 1500805 describes the preparation of Eptifibatide on rink amide resin. In this invention, the thiol of thioalkyl carboxylic acid is protected by triphenylmethyl and guanidine of homoarginine by N,N di-ter butoxycarbinyl protecting groups respectively.

PCT publication no. WO 03/093302 discloses the process for the solid phase synthesis of Eptifibatide comprising of attaching an α-carboxamide amino acid to the solid support 4-methoxy trityl polystyrene resin through its thiol side chain, followed by removing the α-nitrogen protecting group and assembling the peptide chain on the α-nitrogen. thioalkyl carboxylic acid is protected by trityl or by disulphide of thioalkyl carboxylic acid. The process consists of number of steps and uses expensive raw materials.

WO 2009/150657 discloses linear peptide assembly on Rink amide resin, in which thiol groups of cysteine and thioalkyl carboxylic acid are protected by Acm group and guanidine of homoarginine by Pbf group. The assembled peptide is cleaved from the resin to give linear peptide in which thiols of cysteine and thioalkyl carboxylic acid are protected by Acm group. The linear peptide is oxidized by mild oxidation reagent iodine leading to afford Eptifibatide which is not free from forming iodinated impurities in which Trp of the linear peptide gets oxidized and forms byproducts.

US20080182781 discloses that the oxidation of open chain peptides containing free and/or certain types of protected sulfhydryl groups with iodine in, e.g. methanol or acetic acid which is further explained in the CRC Handbook of Neurohypophyseal Hormone analogs, Vol. 1, Part 1; Jost, K., et al., Eds., CRC Press, Boca Raton, Fla. 1987, p. 31. Iodine, however, is not without drawback as a cyclization agent. For instance, tryptophan moieties present in peptide substrates are at risk of being iodinated, making the balance between full conversion of starting materials and minimizing side reactions a delicate one, which in turn impacts product purity.

US publication no. US 2010/0125050 claims a process for manufacturing Eptifibatide which comprises subjecting a solution of Eptifibatide in a solvent to a concentration step wherein the pH of the solution is less than or equal to 7. Preferably the concentration step is evaporation step and the concentration is carried out at the temperature of about 30° C. which avoids usage of higher temperatures.

None of the prior art processes teach about the purity of the crude peptide, lowering the inbuilt process impurities, leading to a robust process with minimal cysteine racemization, higher resolution of the active from the impurities, lower consumption of the organic solvents like ethanol. The present invention describes the complete substitution of the organic nitriles like acetonitriles, enhanced efficiency of the process by increasing the binding capacity of the column during purification and polishing. The use of a combination coupling solvent to minimize cysteine racemization, minimal formation of di-glycine Eptifibatide by controlling molar excess of amino acid addition and proper capping of the N-terminal nitrogen, acid-labile protection of side chain by orthogonal protecting group, avoiding harsh acidic conditions by employing cleavage cocktails using proper scavengers like dithiothreitol, avoiding isolation of SH Eptifibatide by using hydrogen peroxide for faster oxidation is discussed in the present invention.

One embodiment of the invention is use of large scale preparation of Eptifibatide (Formula 1) by Fmoc solid phase synthesis technique, Formula 1 the said process comprising:
a) assembling a peptide chain consisting of six amino acids and a thioalkyl carboxylic acid in a required sequence on a solid support resin by coupling to one another by peptide bonds to obtain a peptide bound resin as given below Mpa(trt)-Har(Pbf)-Gly-Asp(Otbu)-Trp-Pro-Cys(trt) Resin wherein the coupling of cysteine to the resin employs a combination of coupling solvents to reduce cysteine racemization;
b) cleaving from the resin and deprotecting all the protecting groups with 87.5% TFA, 2.5% TIS, 5% DTT and 5% $H_2O$ to give SH-Eptifibatide
c) treating the peptide with hydrogen peroxide leading to instant oxidation obtaining Eptifibatide of formula 1;
d) purifying the crude Eptifibatide of step c) by RP-HPLC to >99% purity by using C1-C4 alcohol wherein the binding capacity of C1-C4 alcohol is 3-5 fold over organic nitrile used.

Another embodiment of the invention is a process comprising the steps of:
a) Manufacturing crude Eptifibatide by coupling of first Fmoc protected cysteine to the solid support using a combination of coupling solvent;
b) assembling the heptapeptide on the solid support, deprotecting, cleaving and oxidizing the heptapeptide to cyclic Eptifibatide using hydrogen peroxide;
c) purifying and polishing the crude Eptifibatide to a purity of >99% by chromatography using C1-C4 alcohols wherein the binding capacity of peptide to silica increases by 3-5 fold;
d) buffer exchanging to adjust the acetate concentration and lyophilizing the Eptifibatide acetate.

Still another embodiment of the invention is use of Fmoc-Har(Pbf)-NH2 group and a simplified process for cost-effective synthesis of the same.

Still another embodiment of the invention is complete substitution of organic nitriles with C1-C4 alcohols for recovery of >90% with >97% purity or more specifically ≥99% purity.

Still another embodiment of the process is efficient use of ethanol/water phase for efficient resolution of impurities from the active using optimized gradient programme for chromatography.

Still another embodiment is obtaining a purity of Eptifibatide of >99% with a recovery of about 20 to 90%.

It should be understood that the following examples described herein are for illustrative purposes only and that various modifications or changes apparent to those skilled in the art are to be included within the spirit and purview of the present invention and the scope of the appended claims.

EXAMPLES

Example (1)

Synthesis

The peptide was synthesized as peptide amide by solid phase peptide synthesis technology on rink amide resin using Fmoc chemistry.

TABLE 1

| Instrument | CS936, Peptide synthesizer |
|---|---|
| Resin | Rink resin (0.58 mm/g) |
| Side chain protecting Groups | Asp-OBut; Homoarg-(pbf); Cys-Trt; Mpr-Trt. |
| Activator | HBTU/NMM |
| Solvent | Dimethyl Formamide |

Figure 1:
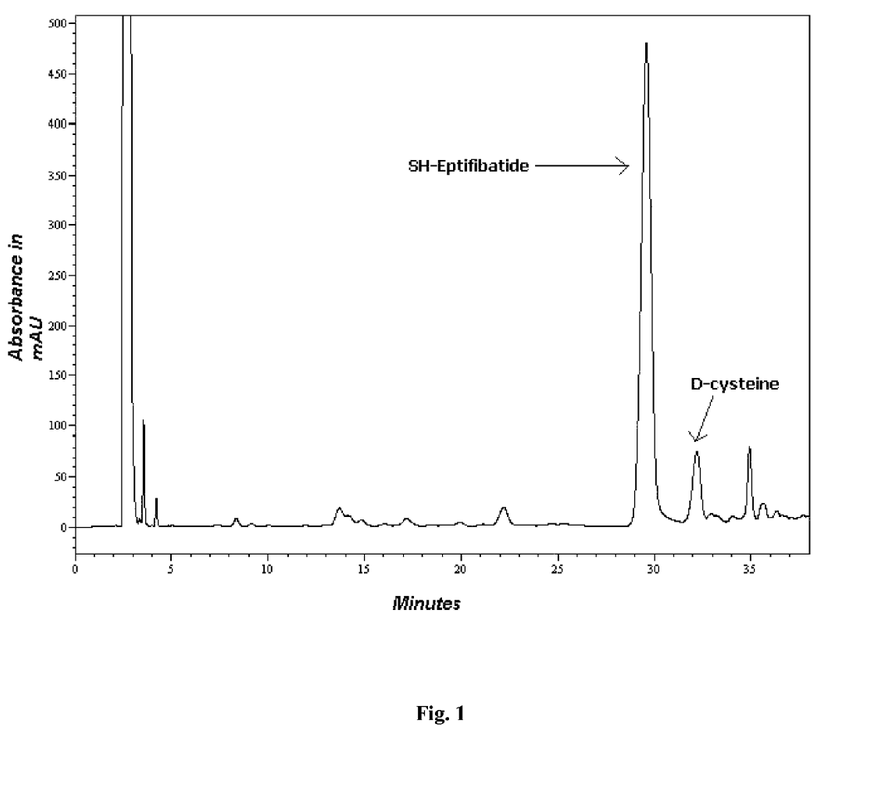
FIG. 1: Analytical RP-HPLC profile of SH-Eptifibatide crude synthesized using only DMF for cysteine coupling.
Figure 2:
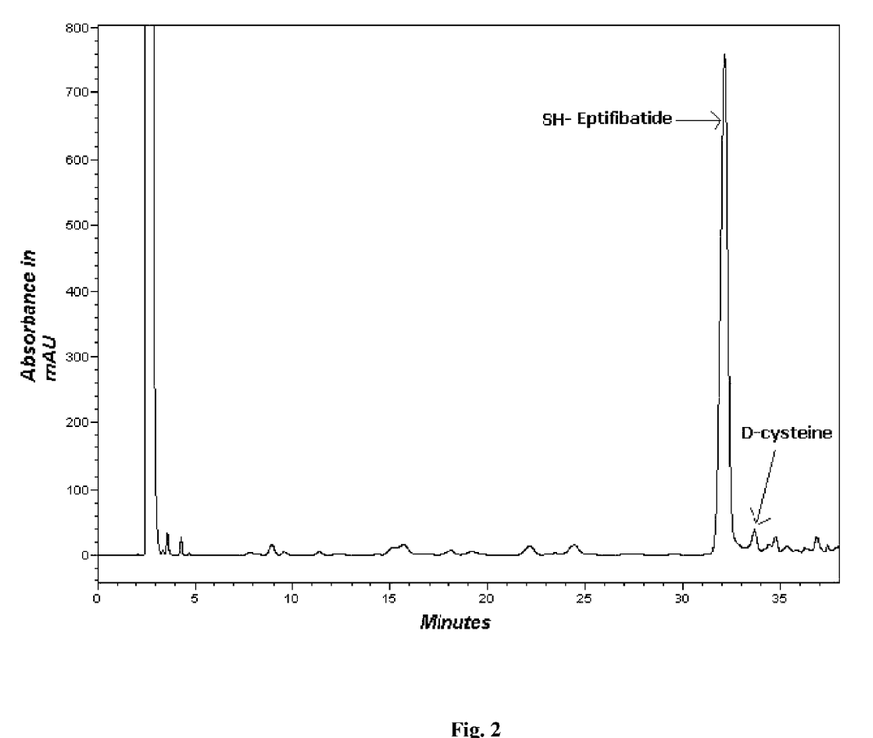
FIG. 2: Analytical RP-HPLC profile of SH-Eptifibatide crude synthesized using DMF:DCM (1:1) for cysteine coupling

The resin (17.24 g-rink amide resin) was transferred to the reaction vessel of the CS936. The attachment of the first amino acid, viz cysteine was carried out using 2 strategies to reduce its racemization.
1. Only DMF as a coupling solvent (FIG. 1)
2. Combination of coupling solvent i.e. DMF/DCM. (FIG. 2)

The preactivation was carried out by dissolving the amino acid in the coupling solvent along with NMM and HBTU. The remaining amino acids were coupled using only DMF as the coupling solvent. A 2 time excess of the amino acid with respect to the mmole of resin was used for synthesis. Each coupling was for 45-60 min. After the couplings were complete, resin was washed with DMF, DCM & dried under vacuum.

TABLE 2

| Coupling solvent | Purity of crude SH Eptifibatide | Percentage of D-Cysteine EPTI impurity |
|---|---|---|
| DMF | 68.8% | 8.3% |
| DMF/DCM | 73.8% | 2.4% |

Example (2)

Cleavage

Figure 3:
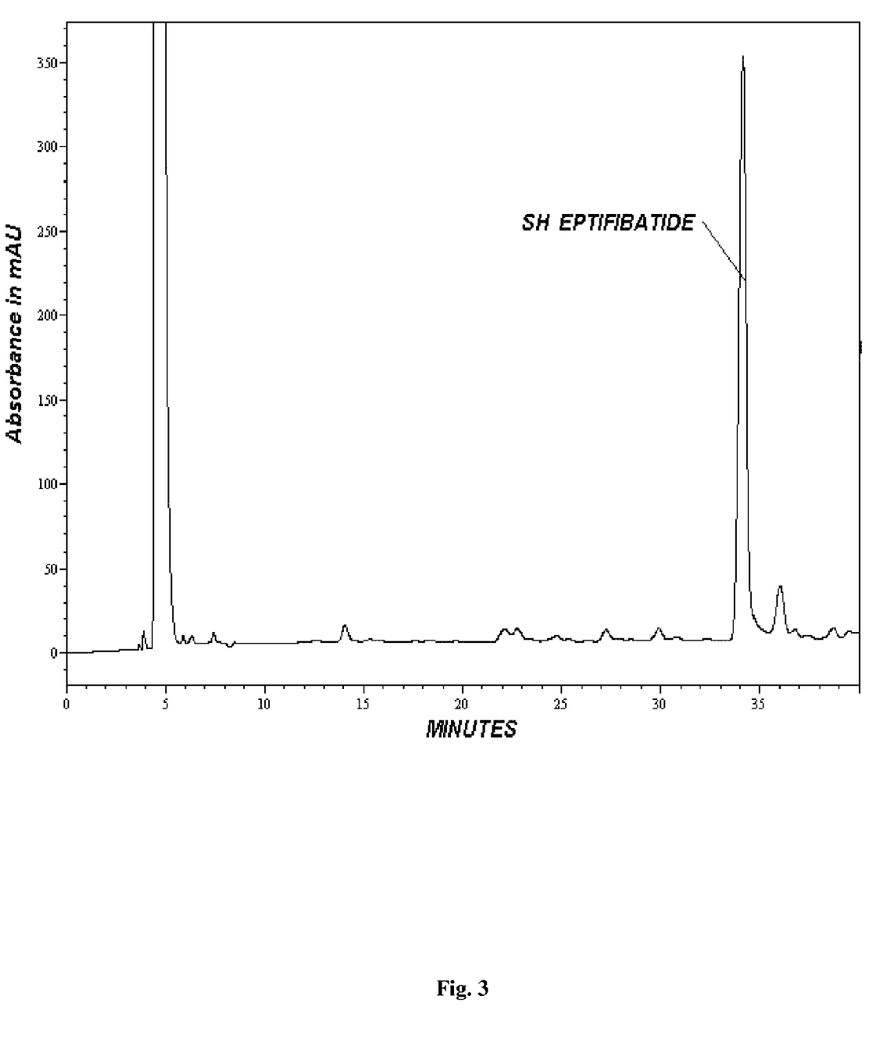
FIG. 3: Analytical RP-HPLC profile of SH-Eptifibatide crude using cleavage cocktail without DTT.
Figure 4:
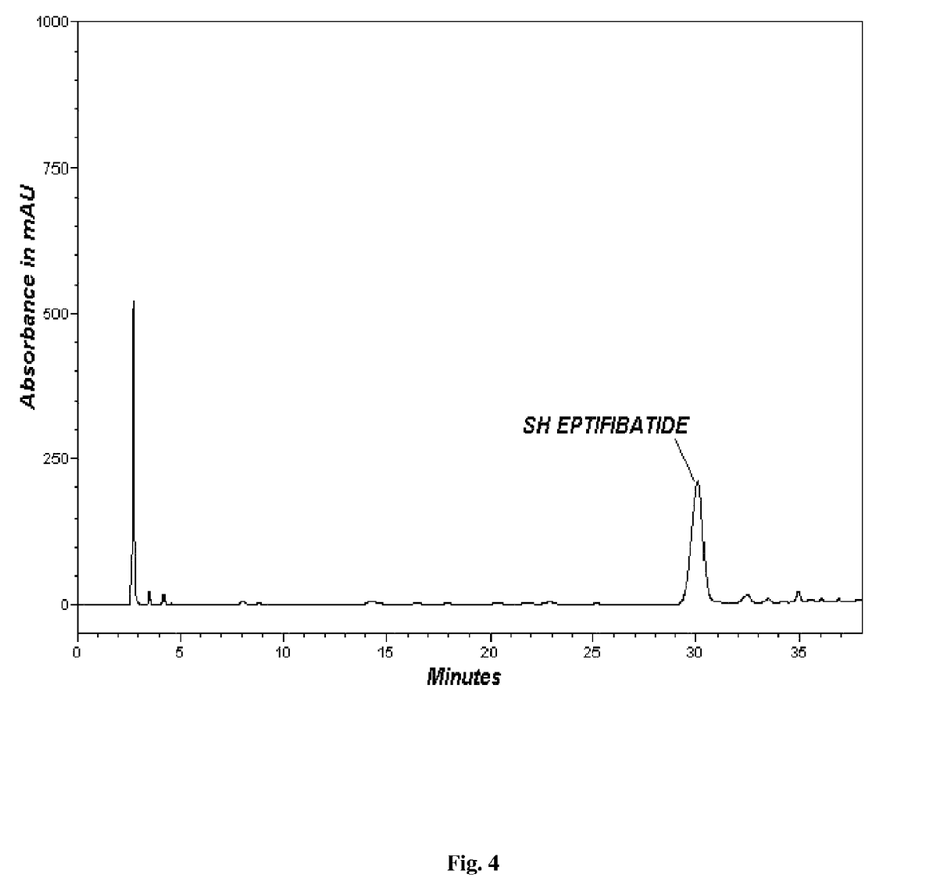
FIG. 4: Analytical RP-HPLC profile of SH-Eptifibatide crude using cleavage cocktail with DTT

Assembled peptide resin (34 g) was treated with different cleavage cocktail (680 ml) each consisting of (1) 95% TFA, 2.5% TIS and 2.5% water or (2) 87.5% TFA, 2.5% TIS, 5% DTT and 5% water for 1.5-2 hrs at R.T. The reaction mixture was filtered and TFA was distilled out on Rotavap. Precipitation of the peptide was carried out at −20° C. by addition of cold diisopropyl ether (700 ml), with stiffing. The crude peptide precipitate in the solvent was let to stand at −20° C. overnight. Isolated the peptide by filtering followed by cold solvent wash. The crude SH Eptifibatide precipitate was dried under vacuum with the yield of 10.0 g having the purity of 61.5% with 95% TFA, 2.5% TIS and 2.5% water (FIG. 3) and the yield of 10.0 g having the purity of 82.0% with 87.5% TFA, 2.5% TIS, 5% DTT and 5% water (FIG. 4).

Example (3)

Purification of SH-Eptifibatide Using 0.1% TFA and Ethanol 250 mg of crude SH-Eptifibatide purified by RPHPLC using Ethanol and 0.1% TFA in water as mobile phase on a C18 column (250×10 mm) with a flow rate of 2.4 ml/min. The purification method consisted of a combination of step and liner gradients yielding a purity of >90%.

Example (4)

Oxidation of SH-Peptide to Eptifibatide Using $H_2O_2$

Oxidation was carried out on purified SH-Eptifibatide in the HPLC elution buffer, 60 ml (0.1% TFA/ethanol) diluted 3 times with water in a vol of 180 ml. The pH was adjusted to 7-9 with $NH_3$, followed by addition of $H_2O_2$ (≥10 times excess with respect to crude SH-peptide) in aliquotes and stirred for 30-60 mins. The reaction was monitored by Ellman Test and RP-HPLC.

Example (5)

RP-HPLC Loading of Peptide to the Column

Binding study for preparative load was carried out by loading a fixed quantity of Eptifibatide in 0.1% TFA containing 4-8% ethanol and 4-8% acetonitrile respectively on C18 column (250×10 mm), with a flow rate of 2.4 ml/min. The flow through during the loading was collected and analyzed for the presence of Eptifibatide in it. The Eptifibatide bound to the silica was later eluted with a higher concentration of the organic solvent and was quantitated in terms of mg/ml. With 4-8% ethanol the said concentration upto 5.0 mg of Eptifibatide/ml of silica could be loaded and with 4-8% acetonitrile the binding was only about 0.8-1.2 mg of Eptifibatide/ml of silica. The binding of Eptifibatide for preparative scale purification with ethanol is thus approx 3.6 fold higher as compared to that with acetonitrile.

Also, the peptide loading with respect to preparative scale on RPHPLC column in order to get optimum resolution and thus optimum purification is almost double with ethanol as compared to that with acetonitrile Eptifibatide binding on a column with different organic solvents:

TABLE 3

| Organic Solvent | Quantity of Eptifibatide loaded | Loading folds |
|---|---|---|
| Acetonitrile | 15 g | X |
| Ethanol | 30 g | 2X |

Compared to acetonitrile, ethanol as a solvent gives 33% cost reduction as calculated on basis of the above data.

Example (6)

Purification of Eptifibatide Using 0.1% TFA and Ethanol

Eptifibatide was purified using ethanol and 0.1% TFA in water on a C-18 (250×10 mm) column with a recovery of >90.0% having the purity of >99.0%

Example (7)

Figure 5:
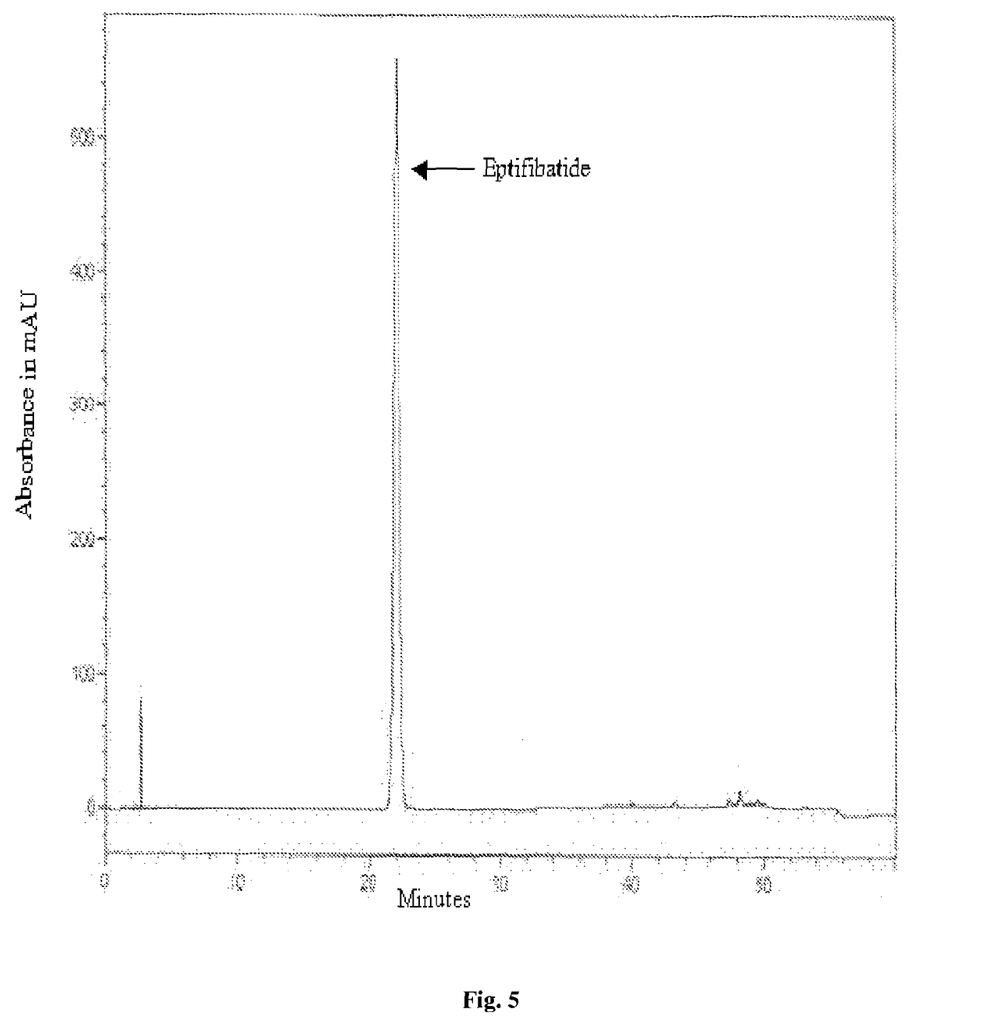
FIG. 5: Analytical RP-HPLC profile of Eptifibatide after lyophilization.

Formation of Eptifibatide Acetate Using Ammonium Acetate/Acetic Acid and Ethanol The counterion TFA was exchanged with acetate by using ammonium acetate/acetic acid and ethanol in water on a C-18 column (250 mm×10 mm). The Peptide fractions were subjected to reverse osmosis and Rotary evaporation for removal of ethanol and concentration. The concentrated material (10-50 mg/ml) was subjected to lyophilization to give the yield of >90.0% having the purity of >99.0% (FIG. 5).

The above discussed sequence therefore has the following sequence listing:

SEQ. ID No. 1

Har(Pbf)-Gly-Asp(Otbu)-Trp-Cys(trt)

We claim:

1. A process for the synthesis of Eptifibatide by Fmoc solid phase synthesis technique, Formula 1 the said process comprising:

a) assembling a peptide chain consisting of six amino acids and a thioalkyl carboxylic acid in a required sequence on a solid support resin by coupling to one another by peptide bonds to obtain a peptide bound resin as given below:

Mpa(trt)-Har(Pbf)-Gly-Asp(Otbu)-Trp-Pro-Cys(trt)
Resin wherein the coupling of cysteine to the resin employs a combination of coupling solvents comprising DMF and DCM in the ratio in the range of 99:1 to 1:99;

b) cleaving from the resin and deprotecting all the protecting groups with 87.5% TFA, 2.5% TIS, 5% DTT and 5% $H_2O$ to give SH-Eptifibatide with a purity of 82%;

c) treating the peptide with hydrogen peroxide leading to instant oxidation obtaining Eptifibatide of formula 1;

d) purifying the crude Eptifibatide of step c) by RP-HPLC to >99% purity by using C1-C4 alcohol wherein the binding capacity of C1-C4 alcohol is 3-5 fold over organic nitrile used.

2. The process of claim 1, wherein the coupling solvent combination, DMF:DCM is used in the ratio of 50:50.

3. The process of claim 1, wherein the C1-C4 alcohol used is selected from a group consisting of methanol, ethanol and isopropanol.

4. The process of claim 3, wherein the C1-C4 alcohol used is ethanol.

* * * * *

SEQUENCE LISTING

```
<160> NUMBER OF SEQ ID NOS: 1

<210> SEQ ID NO 1
<211> LENGTH: 6
<212> TYPE: PRT
<213> ORGANISM: Artificial Sequence
<220> FEATURE:
<223> OTHER INFORMATION: completely sythesized
<220> FEATURE:
<221> NAME/KEY: DISULFID
<222> LOCATION: (1)..(6)
<220> FEATURE:
<221> NAME/KEY: MOD_RES
<222> LOCATION: (1)..(1)
<223> OTHER INFORMATION: Homoarginine
<220> FEATURE:
<221> NAME/KEY: MOD_RES
<222> LOCATION: (1)..(1)
<223> OTHER INFORMATION: 2,2,4,6,7-pentamethyldihydrobenzofuran-
      5-sulfonyl
<220> FEATURE:
<221> NAME/KEY: MOD_RES
<222> LOCATION: (3)..(3)
<223> OTHER INFORMATION: O-t-butyl
<220> FEATURE:
<221> NAME/KEY: MOD_RES
<222> LOCATION: (6)..(6)
<223> OTHER INFORMATION: Trityl

<400> SEQUENCE: 1

Arg Gly Asp Trp Pro Cys
1               5
```